US00RE36718E

United States Patent [19]

Mitsuda et al.

[11] E Patent Number: Re. 36,718

[45] Reissued Date of Patent: May 30, 2000

[54] OPTICALLY ACTIVE AMINOALCOHOL DERIVATIVES AND METHOD OF PRODUCING SAME

[75] Inventors: Masaru Mitsuda, Akashi; Shigeo Hayashi, Ichinomiya; Junzo Hasegawa, Akashi; Noboru Ueyama; Takehisa Ohashi, both of Kobe; Masakatsu Shibasaki, Mitaka, all of Japan

[73] Assignee: Kaneka Corporation, Osaka, Japan

[21] Appl. No.: 09/280,853

[22] PCT Filed: Jun. 29, 1994

[86] PCT No.: PCT/JP94/01049

§ 371 Date: Jun. 21, 1995

§ 102(e) Date: Jun. 21, 1995

[87] PCT Pub. No.: WO95/01323

PCT Pub. Date: Jan. 12, 1995

Related U.S. Patent Documents

Reissue of:

[64] Patent No.: 5,616,726
Issued: Apr. 1, 1997
Appl. No.: 08/392,826
Filed: Jun. 21, 1995

[30] Foreign Application Priority Data

Jun. 29, 1993 [JP] Japan ..... 5-159597
Feb. 24, 1994 [JP] Japan ..... 6-052829

[51] Int. Cl.[7] ..... C07C 215/28

[52] U.S. Cl. ..... 548/475; 560/23; 564/186

[58] Field of Search ..... 548/475; 560/23; 564/186

[56] References Cited

U.S. PATENT DOCUMENTS 4,370,318 1/1983 Umezawa et al. ..... 424/177
5,475,138 12/1995 Pal et al. ..... 564/342

FOREIGN PATENT DOCUMENTS 55-45604 3/1980 Japan .
58-23654 2/1983 Japan .
63-8346 1/1988 Japan .
2-17165 1/1990 Japan .
2-59545 2/1990 Japan .

*Primary Examiner*—Johann Richter
*Assistant Examiner*—Jane Oswecki
*Attorney, Agent, or Firm*—Pollock, Vande Sande & Amernick

[57] ABSTRACT

An object of the present invention is to provide a safe method of commercially producing optically active aminoalcohol derivatives, which serve as intermediates for the synthesis of medicinal chemicals such as the immunopotentiating anticancer agent bestatin, in a simple and easy manner in high yields and with high levels of selectivity.

The present invention consists in a method of producing 3-amino-1-nitro-4-phenyl-2-butanol derivatives of the general formula (1)

(1)

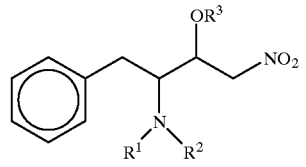

wherein $R^1$ and $R^2$ each independently represents a hydrogen atom or an amino group protecting group, and a method of producing 3-amino-2-hydroxy-4-phenylbutyric acid derivatives derivable therefrom.

24 Claims, No Drawings

OPTICALLY ACTIVE AMINOALCOHOL DERIVATIVES AND METHOD OF PRODUCING SAME

Matter enclosed in heavy brackets [ ] appears in the original patent but forms no part of this reissue specification; matter printed in italics indicates the additions made by reissue.

This application is a National Stage application of PCT/JP94/01049 filed Jun. 29, 1994 and published as WO 95/01323 on Jan. 12, 1995.

TECHNICAL FIELD

The present invention relates to 3-amino-1-nitro-4-phenyl-2-butanol derivatives of the general formula (1) shown below and a method of producing 3-amino-2-hydroxy-4-phenylbutyric acid derivatives of the general formula (11) shown below. An optically active isomer of 3-amino-2-hydroxy-4-phenylbutyric acid (hereinafter referred to as phenylnorstatine) obtainable from a compound of general formula (11) serves as a starting compound for the synthesis of the immunopotentiating anticancer agent bestatin [formula (12)] [Journal of Antibiotics, 29, 600 (1976)] and for the synthesis of the HIV protease inhibitor KNI-227 [formula (13)] (Japanese Kokai Publication Hei-5-170722). Therefore, the compounds provided by the present invention are useful as intermediates of medicinal chemicals.

(1)

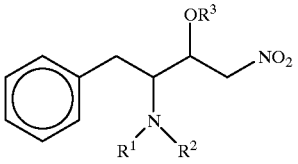

(11)

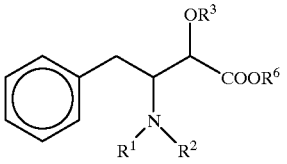

In the above formulas, $R^1$ and $R^2$ each independently represents a hydrogen atom or an amino group protecting group, $R^3$ represents a hydrogen atom or a hydroxy group protecting group and $R^6$ represents a hydrogen atom or an alkyl group containing 1 to 6 carbon atoms.

(12)

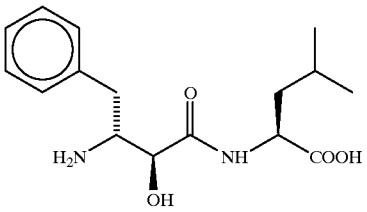

-continued (13)

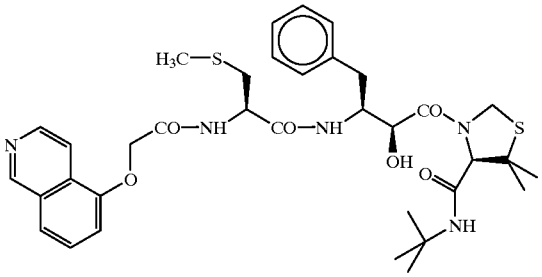

BACKGROUND ART

Phenylnorstatine of the formula (14)

(14)

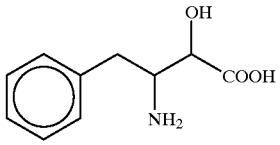

includes four optically active isomers. Among them, the one that can serve as a bestatin intermediate is the (2S,3R)-threo form and the one that can serve as a constituent of KNI- 227 is the (2S,3S)-erythro form. Therefore, a technique of selectively producing only one optical isomer is required for the production of such forms:by a commercially valuable method.

Several methods are known for the stereoselective production of the bestatin intermediate (2S,3R)-phenyl norstatin. Typical of them are those processes that comprise stereoselective addition of a cyanide compound to an (R)-2-amino-3-phenylpropanal derivative derived from D-phenylalanine [Journal of the Chemical Society Chemical Communications, 938 (1989); Synthesis, 703 (1989); European Patent Specification No. 341462; Japanese Kokai Publication Hei-2-17165]. From the industrial viewpoint, however, these processes pose a problem in that the use of a highly toxic cyanide compound is inevitable.

Other methods known include the process comprising degradation of an optically active 2-azetidone derivative obtained via [2+2] cycloaddition of a chiral imine and a ketene compound [Tetrahedron Letters, 31, 3031 (1990)], and the process comprising stereoselective alkylation and stereoselective amination of a chiral glyoxylate [Journal of Organic Chemistry, 54, 4235 (1989)]. However, these methods involve a number of steps, hence are complicated from the procedural viewpoint.

Further methods known comprise stereoselectively alkylating a malic acid ester, selectively amidating one of the carboxyl groups and subjecting the amidation product to Curtius type rearrangement to give optically active phenylnorstatine [European Patent Specification No. 379288; Tetrahedron Letters, 33, 6803 (1992)]. These methods, however, use lithium hexamethyldisilazane, which is an expensive base, and a toxic lead compound, among others, hence are not suited for commercial production.

On the other hand, few methods are known for the stereoselective production of (2S,3S)-phenylnorstatine derivatives. A technique is known which comprises erythro-selective addition of trimethylsilylcyanide to (S)-2-dibenzylamino-3-phenylpropanal in the presence of a Lewis acid [Tetrahedron Letters, 29, 3295 (1988)]. It appears possible to synthesize (2S,3S)-phenylnorstatine by applying this technique. However, the use of a toxic cyanide compound is inevitable in this case, too, and it is difficult to deprotect the dibenzyl protective group.

Another conceivable process making use of the above-mentioned method of selectively synthesizing (2S,3R)-phenylnorstatine derivatives might comprise selectively synthesizing the (2R,3S) form and inverting the configuration of the position 2 by tile per se known method [Journal of the American Chemical Society, 71, 110 (1949)] to give the (2S,3S) form. However, this process involves a large numbers of complicated procedural steps and therefore cannot be used commercially.

Furthermore, Japanese Kokai Publication Hei-2-59545 describes a method of producing 3-amino-4-cyclohexyl-1-nitro-2-butanol derivatives structurally similar to the compounds of the present invention, namely 3-amino-1-nitro-4-phenyl-2-butanol derivatives. However, the method described there is directed only to threo-selective synthesis and the reaction selectivity is as low as 1:1 to 2:1, rendering the method unsatisfactory.

DISCLOSURE OF THE INVENTION

Under these circumstances, it is an object of the present invention to provide synthetic intermediates for producing only one of the four optical isomers of the above-mentioned phenylnorstatine in an efficient, simple and hazard-free manner as well as a relevant method of production.

The present inventors made intensive investigations in an attempt to accomplish this object and, as a result, found that all optically active isomers of optically active phenylnorstatine derivatives (11) can efficiently be produced by a process representable by the following (Flow I). At the same time, they obtained important intermediates for said process. On the basis of these results, they have completed the present invention.

(Flow I)

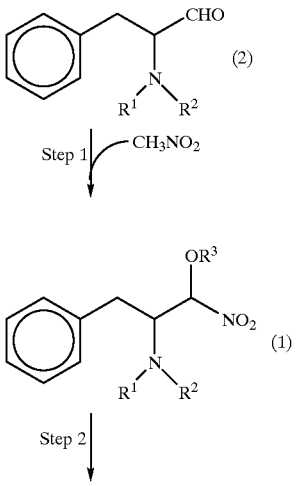

-continued

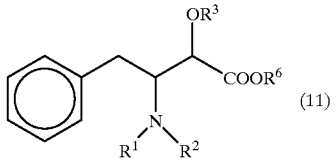

In the above formulas, $R_1$ and $R^2$ each independently represents a hydrogen atom or an amino group protecting group, $R^3$ represents a hydrogen atom or a hydroxy group protecting group and $R^6$ represents a hydrogen atom or an alkyl group containing 1 to 6 carbon atoms.

The production process represented by the above (Flow I) is a technique of obtaining phenylnorstatine derivatives (11) by causing nitromethane to stereo selectively add to an optically active aminoaldehyde derivative (2) in the presence of a base and treating the resulting 3-amino-1-nitro-4-phneyl-2-butanol derivative (1) with an acid to convert the nitromethyl group to a carboxyl group, with the configurations positions 2 and 3 being retained.

The 3-amino-1-nitro-4-phenyl-2-butanol derivatives mentioned above are novel compounds that have not yet been described in the literature. They are substances discovered for the first time by the present inventors.

The amino group protecting group to be employed in the practice of the present invention may be any of the conventional ones provided that it is not affected under the reaction conditions in step 1 of (Flow I). Thus, it includes acyl type protective groups such as formyl, acetyl, trifluroacetyl, benzoyl, pivaloyl and phthaloyl, urethane (carbamate) type protective groups such as benzyloxycarbonyl, t-butoxycarbonyl, isopropoxycarbonyl, ethoxycarbonyl and methoxycarbonyl, substituted alkyl groups such as benzyl, p-methoxybenzyl and triphenylmethyl, and, further, p-toluenesulfonyl, benzenesulfonyl, trifluoromethanesulfonyl, trimethylsilyl, t-butyldimethylsilyl, t-butyldiphenylsilyl, triphenylsilyl and tile like.

Both the (R) and (S) forms of the starting aminoaldehyde derivatives (2) can be readily synthesized, via per se known 3 or 4 steps, from optically active phenylalanine, which is readily available (Flow II).

(Flow II)

(2)

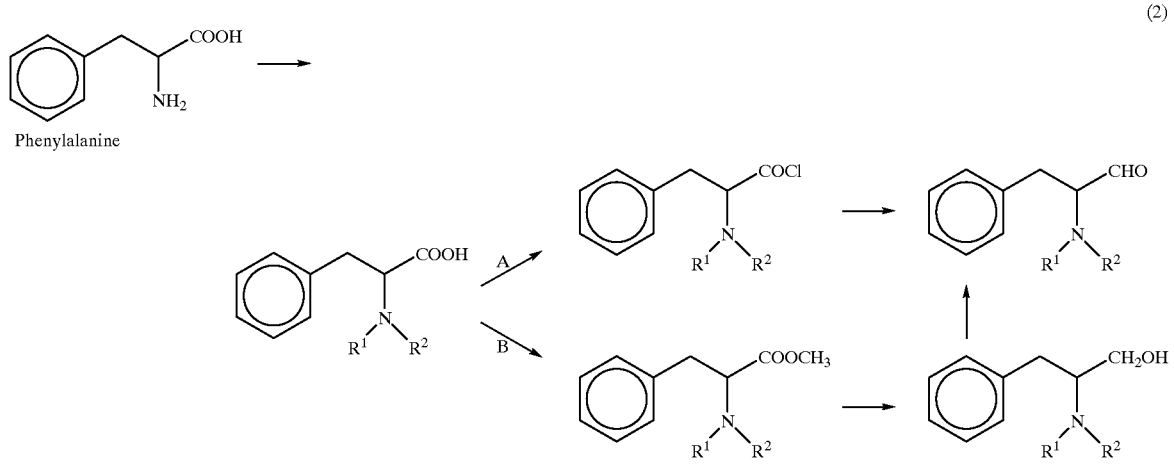

In the above formulas, $R^1$ and $R^2$ each independently represents a hydrogen atom or an amino group protecting group.

The amino group can easily be protected with various amino group protecting groups by the methods described in a monograph (T. W. Greene, P. G. M. Wuts: Protective Groups in Organic Synthesis, 2nd edition, John Wiley & Sons, Inc., 1991; or elsewhere).

For instance, when the amino group protecting group $R^1$ plus $R^2$ in (Flow II) is a phthaloyl group, the aminoaldehyde derivative (2) can be obtained by treating phthaloylphenylala nine with thionyl chloride to give the corresponding acid chloride, as indicated by A in (Flow II), and then reducing the acid chloride with tri-t-butoxyaluminum hydride [Tetrahedron, 30, 4233 (1974)].

When, in (Flow II), $R^1$ is a hydrogen atom and $R^2$ is a urethane or carbamate type protective group ($R^2$=COOR where R is benzyl, t-butyl, isopropyl or a like alkyl group) generally used as an amino group protecting group, the derivative (2) can be prepared by converting the N-protected phenylalanine to the methyl ester, as indicated by B in (Flow II), then reducing the ester to the corresponding alcohol and oxidizing the latter with dimethyl sulfoxide [e.g. Journal of Organic Chemistry, 57, 5692 (1992)]. In the first step of the process of the present invention, the thus-prepared aminoaldehyde derivative (2) is reacted with nitromethane in the presence of a base in the manner of nitroaldol reaction (Henry reaction) for the synthesis of the 3-amino-1-nitro-4-phenyl-2-butanol derivative (1).

The base to be used in,this first step includes organic bases such as triethylamine, pyridine, diethylamine and diisopropylethylamine; alkali metal and alkaline earth metal hydroxides such as sodiumhydroxide, lithium hydroxide, potassium hydroxide, magnesium hydroxide and barium hydroxide; magnesium alkoxides of the general formula (7)

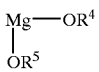

(7)

wherein $R^4$ and $R^5$ each represents an alkyl group containing 1 to 6 carbon atoms, such as magnesium isopropoxide, magnesium methoxide, magnesium ethoxide and magnesium butoxide; and zirconium t-butoxide and other metal alkoxides showing basicity, for example alkali metal, alkaline earth metal and rare earth alkoxides such as sodiunm methoxide, potassium t-butoxide and lanthanum t-butoxide.

Also usable as the base are compounds of the general formula (8)

$$R^7Li \quad (8)$$

wherein $R^7$ is an aryl group or an alkyl group containing 1 to 6 carbon atoms, such as n-butyllithium, sec-butyllithium, methyllithium and phenyllithium; isopropylmagnesium bromide and alkylmetals such as diethylzinc; and metal hydrides such as sodium hydroxide and calcium hydroxide. In addition, such compounds as lithium diisopropylamide, lithium hexamethyldisilazane, lithium cyclohexylisopropylamide, sodium amide and potassium amide can also be used as the base in this step.

Further, use can also be made of complexes prepared from a compound of the general formula (9)

$$MX_3 \quad (9)$$

wherein M is a rare earth atom and X is a halogen atom, and 1,1'-bi-2-naphthol or the lithium salt thereof, for example the complex prepared from lanthanum trichloride and (R)-1,1'-bi-2-naphthol [Tetrahedron Letters, 34, 851 (1993); Journal of American Chemical Society, 114, 4418 (1992)] and the like.

Still further, complexes prepared from a compound of the general formula (10)

$$M(OR^8)_3 \quad (10)$$

wherein M is a rare earth atom and $R^8$ is a substituted alkyl group containing 1 to 8 carbon atoms, and 1,1'-bi-2-naphthol or the lithium salt thereof, for example the complex prepared from lanthanum triisopropoxide and the lithium salt of (R)-1,1'-bi-2-naphthol [Journal of American Chemical Society, 115, 10372 (1993)] and the like can also be used.

The term "rare earth atom" as used herein means an atom of the 4th to 6th period of the group IIIB of the periodic table and includes, within the meaning thereof, not only lanthanum but also praseodymium, neodymium, europium, gadolinium, dysprosium, erbium, ytterbium, yttrium and the like.

The use, in the first step, of the base in a catalytic amount of about 0.01 to 0.1 mole per mole of the aminoaldehyde derivative (2) is sufficient for driving the reaction to completion. However, for the purpose of completing the reaction under mild conditions and in a short period of time, the base may be used in an amount of 0.1 to 1.2 molar equivalents. Even a large excess (2 molar equivalents or more) of the base may be used without producing any adverse effects, without causing any side reactions.

Any solvent may be used as the reaction solvent provided that it will not react with the raw materials under the reaction conditions. For example, mention may be made of water; alcohol solvents such as methanol, ethanol, isopropanol, t-butanol and ethylene glycol; ethereal solvents such as diethyl ether, tetrahydrofuran (hereinafter, THF), 1,4-dioxane, glyme and diglyme; halogenated hydrocarbon solvents such as methylene chloride, chloroform, 1,1,1-trichloroethane and monochlorobenzene; hydrocarbon solvents such as benzene, toluene, n-hexane and n-pentane; and fatty acid esters such as ethyl acetate and methyl acetate. Polar solvents such as dimethyl sulfoxide and N,N-dimethylformamide may also be used. Furthermore, nitromethane itself may be used also as the solvent. Two or more of the solvents mentioned above may be used in admixture.

The above-mentioned solvent is used preferably in an amount of 5 to 20 volumes per weight of the aminoaldehyde derivative (2). Nitromethane, when used in an amount of 1.0 to 1.5 molar equivalents, can bring the reaction to completion in high yields. Even when it is used in large excess, for example in an amount of 5 to 20 molar equivalents, no adverse effects nor side reactions will be produced or induced. After completion of the reaction, the excess nitromethane can be recovered in the step of removing the reaction solvent by distillation and the recovered nitromethane, as such, can be reused for the reaction.

The present reaction can be carried out at a temperature between −100° C. and the refluxing temperature of the reaction solvent.

The configuration of the carbon atom at position 3 (to which the amino group is attaching) in the 3-amino-1-nitro-4-phenyl-2-butanol derivative (1) obtained as a result of the present reaction inherits the configuration of the aminoaldehyde derivative (2) used as the starting material as it is. Thus, when the (S) form of the above compound (2) is used as the starting material, the product (1) will have the (S) configuration at position 3. When the (R) form is used as the starting material, the product (1) will have the (R) configuration at position 3.

In the present reaction, the addition reaction of nitromethane occurs either erythro-selectively or threo-selectively depending on the amino group protecting group selected. While, in ordinary cases, the product of nucleophilic addition to such an aldehyde as one having the general formula (2) is an epimeric mixture with respect to the configuration of the carbon atom to which a hydroxyl group is attaching, it is possible in the present reaction to cause preferential formation of a product (1) having the (R) or (S) configuration with respect to the carbon atom at position 2 by selecting an appropriate amino group protecting group.

Thus, for example, when a phthaloyl group is selected as the amino group protecting group for the compound of general formula (2), erythro-selective addition occurs in the present reaction. Therefore, when the compound of general formula (2) is (S)-phthaloylphenylalaninal, the reaction selectively gives the product (1) in [(2S,3S)] (*2R3S*) form. When the compound (2) is (R)-phthaloylphenylalaninal, the product (1) is obtained selectively in (2S,3R) form.

When a t-butoxycarbonyl group (BOC) is employed as the amino group protecting group for the compound of general formula (2), threo-selective addition occurs in the present reaction. Therefore, when the compound of general formula (2) is (S)-BOC-phenyalaninal, the reaction selectively gives the product (1) in [(2R,3S)] (*2S,3S*) form. When the compound (2) is (R)-BOC-phenylalaninal, the reaction selectively gives the product (1) in (2S,3R) form.

Thus, the technique of the present invention makes it possible to selectively produce any arbitrary one of the four optical isomers of the 3-amino-1-nitro-4-phenyl-2-butanol derivative (1) and of the phenylnorstatine derivative (11) derivable from said derivative (1) by merely selecting the configuration of the starting material aminoaldehyde derivative (2) and the amino group protecting group.

The degree of stereoselectivity (threo- or erythro-selectivity) of the present reaction depends also on the base employed.

When an asymmetric base catalyst is used in the present reaction, a high degree of stereoselectivity can be obtained owing to the effect of double asymmetric induction. For example, the above-mentioned complexes of a rare earth halide or rare earth alkoxide with optically active 1,1'-bi-2naphthol or the lithium salt thereof, which are known as catalysts for the asymmteric nitroaldol reaction can be used as the asymmetric base.

The reaction mixture after completion of the reaction is washed with a dilute acid and water, and the solvent and unreacted nitromethane are distilled off under reduced pressure to give the product of general formula (1) in crude form. The unnecessary optical isomer of compound (1) contained in the crude product can be removed by such purification means as recrystallization or silica gel column chromatography. Since purification can also be made in a later step, the product in a mixture form may be submitted as such to the next step.

When the present reaction is carried out in the presence also of an acyl donor, such as an acyl halide or acid anhydride, or an alkylsilyl halide in the reaction mixture, the product is obtained in the form in which the hydroxyl group is protected with the corresponding acyl or silyl group, for instance.

In the thus-obtained compound (1), the hydroxy group protecting group represented by $R^3$ is, for example, an acyl group such as acetyl, benzoyl or pivaloyl, or an alkylsilyl group such as trimethylsily, t-butyldimethylsilyl, t-butyldiphenylsilyl or triphenylsilyl.

In the second step of the process of the present invention, the nitromethyl group of the 3-amino-1-nitro-4-phenyl-2-butanol derivative (1) obtained in the first step is converted to a carboxyl group by acid treatment to give the phenylnorstatine derivative (11), with the configurations at positions 2 and 3 being retained.

When, in the second step, the amino group protecting group $R^1$ and $R^2$ employed are eliminable by acid treatment, amino deprotection can be attained simultaneously with the conversion of nitromethyl to carboxyl.

The acid to be used in the present reaction is a strong acid such as hydrochloric, sulfuric or nitric acid. It is used in an amount of 1 to 100 molar equivalents, preferably 20 to 60 molar equivalents, relative to the 3-amino-1-nitro-4-phenyl-2-butanol derivative (1).

Water is preferred as the reaction solvent and recomendably used in an amount of 5 to 15 volumes relative to the 3-amino-1-nitro-4-phenyl-2-butanol derivative (1). In certain instances, methanol, ethanol, isopropanol, t-butanol or the like may be admixed with water to thereby increase the solubility of the starting material.

The reaction is carried out preferably at a temperature of 80° to 100° C., more preferably 100° C.

Under the most general reaction conditions, the 3-amino-1-nitro-4-phenyl-2-butanol derivative (1) is heated in 12N concentrated hydrochloric acid at 100° C. for at least 24 hours. In most cases, the reaction mixture occurs as a suspension in the early stage of reaction because of insolubility of the compound (1) mentioned above but gradually turns into a homogeneous solution with the progress of the reaction.

After completion of the reaction, the reaction mixture is cooled to room temperature, the insoluble matter is filtered off and the filtrate is concentrated under reduced pressure, whereupon the product phenylnorstatine derivative (11) crystallizes out. Separation of the crystals by filtration at this point of time gives the desired product in pure form. Further evaporation to dryness without collection of said crystals by filtration, followed by recrystallization of the residue can also afford the phenylnorstatine derivative (11) in pure form.

BEST MODES FOR CARRYING OUT THE INVENTION

The following examples illustrate the present invention in further detail but are by no means limitative of the scope of the present invention.

In the examples, the following analytical apparatus were used for various analytical purposes.

Nuclear magnetic resonance spectrometer (NMR): Nihon Denshi model EX-400

Infrared spectrophotometer (IR): Shimadzu model FTIR-8100M Polarimeter ([α]): Horiba Seisakusho model SEPA-200 High-performance liquid chromatograph (HPLC): Shimadzu model LC-9A UV detector: Shimadzu model SPD-6A Data processor: Shimadzu model C-R6A

REFERENCE EXAMPLE 1

Preparation of lanthanum/(R)-1,1'-bi-2-naphthol complex solution

To a suspension of 122.6 mg (0.50 mmol) of anhydrous lanthanum trichloride in 6.0 ml of THF were added, in an argon atmosphere and at room temperature, a lithium binaphthoxide solution in THF [prepared by adding 0.625 ml (1.0 mmol) of a 1.6N n-butyllithium solution in hexane to a solution of 143.2 mg (0.50 mmol) of (R)-1,1'-bi-2-naphthol in 2.5 ml of THF], 48.1 mg (0.50 mmol) of sodium t-butoxide and 99 μl (5.5 mmol) of water in that order. The resultant mixture was stirred at room temperature for 15 hours. The insoluble matter was caused to precipitate by allowing the mixture to stand overnight, and the supernatant was submitted to the reaction proper as a lanthanum/(R)-1,1'-bi-2-naphthol complex solution (0.05 mol/l).

Example 1

Synthesis of [(2S,3S)] (*2R,3S*)-1-nitro-4-phenyl-3-phthaloylamino-2-butanol

To a stirred solution of 559 mg (2.0 mmol) of (S)-3-phenyl-2-phthaloylaminopropanal [synthesized by the method described in Tetrahedron, 30, 4233 (1974)] in 8.0 ml of THF was added 2.17 ml (40 mmol) of nitromethane at 0° C., followed by dropwise addition of 4.0 ml (0.20 mmol) of the lanthanum/(R)-1,1'-bi-2-naphthol complex solution (Reference Example 1, 0.05 mol/l). The resultant mixture was stirred at 0° C. for 2 hours. To the solution were added 2 mol of 1N hydrochloric acid and 10 ml of water. The mixture was extracted with diethyl ether, and the extract was washed with a saturated aquenous solution of sodium chloride and dried over anhydrous sodium sulfate. The solvent was distilled off under reduced pressure and the residue was purified by silica gel column chromatography (eluent; n-hexane-ethyl acetate 8:2) to give 563 mg of [(2S,3S)] (*2R,3S*)-1-nitro-4-phenyl-3-phthaloylamino-2-butanol and 99 mg of [(2R,3S)] (*2S,3S*)-1-nitro-4-phenyl-3-phthaloylamino-2-butanol.

Yield 97%; [(2S,3S): (2R,3S)] (*2R,3S*): (*2S,3S*)=85:15.

[(2S,3S)] (*2R,3S*)-1-Nitro-4-phenyl-3-phthaloylamino-2-butanol:

$[\alpha]_D^{20}$: −146 (C=1.02 in chloroform)

IR (Nujol) ν($cm^{-1}$): 3520, 3480, 1770, 1740, 1700

$^1$H-NMR (400 MHz, $CDCl_3$)δ(ppm): 3.34 (2H, d, J=7.8 Hz), 3.79 (1H, bs), 4.42–4.52 (2H, m), 4.56–4.63 (1H, m), 4.95–5.00 (1H, m), 7.08–7.19 (5H, m), 7.68–7.74 (2H, m), 7.74–7.79 (2H, m)

$^{13}$C-NMR (100 MHz, $CDCl_3$)δ(ppm): 33.6, 55.0, 69.9, 78.2, 123.6, 127.0, 128.6, 128.9, 131.1, 134.5, 136.5, 168.4

[(2R,3S)] (*2S,3S*)-1-Nitro-4-phenyl-3-phthaloylamino-2-butanol:

$[\alpha]_D^{20}$: −117 (C=1.00 in chloroform)

IR (Nujol) ν($cm^{-1}$): 3480, 1770, 1745, 1700

$^1$H-NMR (400 MHz, $CDCl_3$)δ(ppm): 3.29 (2H, d, J=7.8 Hz), 4.37 (1H, bs), 4.40 (2H, d, J=3.9 Hz), 4.67–4.75 (2H, m), 7.15–7.24 (5H, m) , 7.78–7.76 (2H, m), 7.77–7.81 (2H, m)

$^{13}$C-NMR (100 MHz, $CDCl_3$)δ(ppm): 35.1, 55.4, 69.2, 79.0, 123.8, 127.2, 128.8, 129.1, 131.1, 134.7, 136.1, 168.5

REFERENCE EXAMPLE 2

Preparation of lanthanum/(S)-1,1'-bi-2-naphthol complex solution

A lanthanum/(S)-1,1'-bi-2-naphthol complex solution (0.05 mol/l) was prepared in the same manner as in Reference Example 1 using (S)-1,1'-bi-2-naphthol.

Example 2

To a stirred solution of 559 mg (2.0 mmol) of (S)-3-phenyl-2-phthaloylaminopropanal in 8.0 ml of THF was added, at 0° C., 2.17 ml (40 mmol) of nitromethane, followed by dropwise addition of 4.0 ml (0.20 mmol) of the lanthanum/(S)-1,1'-bi-2-naphthol complex solution (Reference Example 2, 0.05 mol/l). The mixture was stirred at 0° C. for 2 hours. To the solution were added 2 ml of 1N hydrochloric acid and 10 ml of water. The mixture was extracted with diethyl ether, and the extract was washed with a saturated aqueous solution of sodium chloride and dried over anhydrous sodium sulfate. The solvent was distilled off under reduced pressure and the residue was purified by silica gel column chromatography (eluent: n-hexane-ethyl acetate 8:2) to give 427 mg of [(2S,3S)] (*2R,3S*)-1-nitro-4-phenyl-3-phthaloylamino-2-butanol and 136 mg of [(2R,3S)] (*2S,3S*)-1-nitro-4-phenyl-3-phthaloylamino-2-butanol. Yield 98%; [(2S,3S):(2R,3S)] (*2R,3S*):(*2S,3S*)=75:25.

Example 3

To a stirred solution of 70 mg (0.25 mmol) of (S)-3-phenyl-2-phthaloylaminopropanal in 1.0 ml of THF was added, at 0° C., 0.27 ml (5 mmol) of nitromethane, followed by dropwise addition of a suspension of 7.1 mg (0.05 mmol) of magnesium diisopropoxide in 1.0 ml of THF. The mixture was stirred at 0° C. for 2 hours. To the solution were added 0.3 ml of 1N hydrochloric acid and 3 ml of water. The mixture was extracted with diethyl ether, and the extract was washed with a saturated aqueous solution of sodium chloride and dried over anhydrous sodium sulfate. The solvent was distilled off under reduced pressure, the residue was analyzed by HPLC, and the yield and the diastereomer ratio of the product were determined. Yield 72%; [(2S,3S):(2R,3S)] (*2R,3S*):(*2S,3S*)=80:20. Conditions of HPLC analysis Column: Finepak C18-5 (Nippon Bunko)

Column temperature: 35° C.

Eluent: water/acetonitrile 55:45

Flow rate: 1:0 ml/min.

Detection wavelength: 210 nm

Examples 4 to 6

The procedure of Example 3 was followed using other metal alkoxide bases. The results obtained are shown in Table 1. In Table 1, tBu denotes a t-butyl group.

TABLE 1

| | Base | Molar equivalents | % yield | [(2S, 3S):(2R, 3S)] (2R, 3S):(2S, 3S) |
|---|---|---|---|---|
| Example 4 | $La(OrBu)_2$ | 0.1 | 88 | 64.36 |
| Example 5 | NaOtBu | 0.2 | 91 | 64:36 |
| Example 6 | KOtBu | 0.2 | 86 | 61:39 |

REFERENCE EXAMPLE 3

Preparation of lanthanum/(R)-1,1'-bi-2-naphthol complex solution

To a solution of 258 mg (0.90 mmol) of (R)-1,1'-bi-2-naphthol in 4.5 ml of THF Was added dropwise 0.56 ml (0.90 mmol) of a 1.6N n-butyllithium solution in hexane, at 0° C. in an argon atmosphere. After completion of the dropping, the temperature was raised to room temperature, 95 mg (0.30 mmol) of powdery lanthanum isopropoxide was added, and the mixture was stirred at room temperature for 15 hours. The insoluble matter was allowed to precipitate and the supernatant was submitted, as a lanthanum/(R)-1,1'-bi-2-naphthol complex solution (0.05 mol/l), to the reaction proper.

Example 7

To a solution of 70 mg.(0.25 mmol) of (S)-3-phenyl-2-phthaloylaminopropanal in 1.0 ml of THF was added 0.27 ml (5 mmol) of nitromethane with stirring at −30° C., followed by dropwise addition of 0.5 ml (0.025 mmol) of the lanthanum/(R)-1,1'-bi-2-naphthol complex solution (Reference Example 3, 0.05 mol/l). The resultant mixture was stirred at −30° C. for 5 hours. To this solution were then added 0.5 ml of 1N hydrochloric acid and 3 ml of water. The mixture was extracted with diethyl ether, and the extract was washed with a saturated aqueous solution of sodium chloride and dried over anhydrous sodium sulfate. The solvent was distilled off under reduced pressure, the residue was analyzed by HPLC in the same manner as in Example 3, and the yield and diastereomer ratio of the product were determined. Yield 83%; [(2S,3S):(2R,3S)] (*2R,3S*):(*2S,3S*)=98:2.

Example 8

To a solution of 70 mg (0.25 mmol) of (S)-3-phenyl-2-phthaloylaminopropanal in 1.0 ml of THF was added 0.27 ml (5 mmol) of nitromethane with stirring at −30° C., followed by dropwise addition of 0.05 ml (0.0025 mmol) of the lanthanum/(R)-1,1'-bi-2-naphthol complex solution (Reference Example 3, 0.05 mol/l). The resultant mixture was stirred at −30° C. for 17 hours. To this solution were then added 0.5 ml of 1N hydrochloric acid and 3 ml of water. The mixture was extracted with diethyl ether, and the extract was washed with a saturated aqueous solution of sodium chloride and dried over anhydrous sodium sulfate. The solvent was distilled off under reduced pressure, the residue was analyzed by HPLC in the same manner as in Example 3, and the yield and diastereomer ratio of the product were determined. Yield 82%; [(2S,3S):(2R,3S)] (*2R,3S*)(*2R,3S*)=96:4.

REFERENCE EXAMPLE 4

A praseodymium/(R)-1,1'-bi-2-naphthol complex (0.05M solution) and a neodymium/(R)-1,1'-bi-2-naphthol complex (0.05M solution) were prepared in the same manner as in Reference Example 1 using praseodymium trichloride ($PrCl_3$) and neodymium trichloride ($NdCl_3$), respectively.

REFERENCE EXAMPLE 5

Preparation of samarium/(R)-1,1'-bi-2-naphthol complex solution

To a suspension of 128 mg (0.50 mmol) of anhydrous samarium trichloride ($SmCl_3$) in 4.0 ml of THF were added, in an argon atmosphere at room temperature, a lithium binaphthoxide solution in THF [prepared by adding 1.25 ml (2.0 mmol) of a 1.6N n-butyllithium solution in hexane to a solution of 286.4 mg (1.0 mmol) of (R)-1,1'-bi-2-naphthol in 4.0 ml of THF], 48.1 mg (0.50 mmol) of sodium t-butoxide and 99 $\mu$l (5.5 mmol) of water, in that order, and the mixture was stirred at room temperature for 15 hours and then allowed to stand overnight to allow the insoluble matter to precipitate. The supernatant solution was submitted to the reaction proper as a samarium/(R)-1,1'-bi-2-naphthol complex solution (0.05 mmol/l).

REFERENCE EXAMPLE 6

The procedure of Reference Example 5 was followed using six rare earth chlorides, namely europium trichloride ($EuCl_3$), gadolinium trichloride ($GdCl_3$), dysprosium trichloride ($DyCl_3$), erbium trichloride ($ErCl_3$), ytterbium trichloride ($YbCl_3$) and yttrium trichloride ($YCl_3$), to give a europium/(R)-1,1'-bi-2-naphthol complex solution (0.05 mmol/l), a gadolinium/(R)-1,1'-bi-2-naphthol complex solution (0.05 mol/l), a dysprosium/(R)-1,1'-bi-2-naphthol complex solution (0.05 mol/l), an erbium/(R)-1,1'-bi-2-naphthol complex solution (0.05 mol/l), an ytterbium/(R)-1,1'-bi-2-naphthol complex solution (0.05 mol/l) and an yttrium/(R)-1,1'-bi-2-naphthol complex solution (0.05 mol/l), respectively.

Examples 9 to 17

To a stirred solution of 70 mg (0.25 mmol) of (S)-3-phenyl-2-phthaloylaminopropanal in 1.0 ml of THF was added, at −50° C., 0.27 ml (5 mmol) of nitromethane, followed by dropwise addition of 0.5 ml (0.025 mmol) of one of the complex solutions prepared in Reference Examples 4 to 6. The resultant mixture was stirred at −50° C. for 72 hours. To this solution were added 0.5 ml of 1N hydrochloric acid and 3 ml of water. The mixture was extracted with diethyl ether, and the extract was washed with a saturated aqueous solution of sodium chloride and dried over anhydrous sodium sulfate. The solvent was distilled off under reduced pressure, and the residue was analyzed by HPLC in the same manner as in Example 3 to determine the yield and diastereomer ratio of the product. The results thus obtained are shown in Table 2.

TABLE 2

| | Complex | % yield | [(2S, 3S):(2R, 3S)] (2R, 3S):(2S, 3S) |
|---|---|---|---|
| Example 9 | Praseodymium/(R)-1,1'-bi-2-naphthol | 53 | 86:14 |
| Example 10 | Neodymium/(R)-1,1'-bi-2-naphthol | 78 | 94:6 |
| Example 11 | Samarium/(R)-1,1'-bi-2-naphthol | 79 | 97:3 |
| Example 12 | Europium/(R)-1,1'-bi-2-naphthol | 72 | 98:2 |
| Example 13 | Gadolinium/(R)-1,1'-bi-2-naphthol | 79 | 95:5 |
| Example 14 | Dysprosium/(R)-1,1'-bi-2-naphthol | 91 | 83:17 |
| Example 15 | Erbium/(R)-1,1'-bi-2-naphthol | 81 | 80:20 |
| Example 16 | Ytterbium/(R)-1,1'-bi-2-naphthol | 89 | 78:22 |
| Example 17 | Yttrium/(R)-1,1'-bi-2-naphthol | 95 | 79:21 |

Example 18

To a stirred solution of 70 mg (0.25 mmol) of (S)-3-phenyl-2-phthaloylaminopropanal in 1.5 ml of THF was added, at 0° C. , 0.27 ml (5 mmol) of nitromethane, followed by dropwise addition of 0.05 ml (0.05 mol) of 1N aqueous sodium hydroxide. The resultant mixture was stirred at 0° C. for 2 hours. To this solution were added 0.3 ml of 1N hydrochloric acid and 3 ml of water. The mixture was extracted with diethyl ether, and the extract was washed with a saturated aqueous solution of sodium chloride and dried over anhydrous sodium sulfate. The solvent was distilled off under reduced pressure and the residue was analyzed by HPLC in the same manner as in Example 3 to determine the yield and diastereomer ratio of the product. Yield 44%; [(2S,3S):(2R,3S)] (*2R,3S*):(*2S,3S*)=72:28.

Examples 19 and 20

The procedure of Example 18 was followed using two other metal hydroxides. The results obtained are shown in Table 3.

TABLE 3

| | Base | Molar equivalents | % yield | [(2S, 3S):(2R, 3S)] (2R, 3S):(2S, 3S) |
|---|---|---|---|---|
| Example 19 | LiOH | 0.2 | 83 | 75:25 |
| Example 20 | KOH | 0.2 | 72 | 66:34 |

Example 21 to 30

(S)-3-Phenyl-2-phthaloylaminopropanal (70 mg, 0.25 mmol) was dissolved in 1.5 ml of a specified solvent, 0.041 ml (0.75 mmol) of nitromethane was added with stirring at 0° C. , 0.063 ml (0.25 mmol) of 4N aqueous lithium hydroxide was added dropwise, and the mixture was stirred at 0° C. for 2 hours. To this solution were added 0.3 ml of 1N hydrochloric acid and 3 ml of water. The mixture was extracted with diethyl ether, and the extract was washed with a saturated aqueous solution of sodium chloride and dried over anhydrous sodium sulfate. The solvent was distilled off under reduced pressure and the residue was analyzed by HPLC in the same manner as in Example 3 to determine the yield and diastereomer ratio of the product. The results thus obtained are shown in Table 4.

TABLE 4

| | Solvent | % yield | [(2S, 3S):(2R, 3S)] (2R, 3S):(2S, 3S) |
|---|---|---|---|
| Example 21 | Dimethoxycthane | 73 | 81:19 |
| Example 22 | Diisopropyl ether | 18 | 68:32 |
| Example 23 | 1,4-Dioxane | 77 | 77:23 |
| Example 24 | t-Buyyl methyl ether | 19 | 70:30 |
| Example 25 | Ethyl acetate | 14 | 76:24 |
| Example 26 | Methanol | 63 | 73:27 |
| Example 27 | Isopropanol | 79 | 76:24 |
| Example 28 | Acetone | 66 | 78:22 |
| Example 29 | Acetonitrile | 49 | 73:27 |
| Example 30 | N,N-Dimethylformamide | 79 | 60:40 |

Example 31

To a stirred solution of 70 mg (0.25 mmol) of (S)-3-phenyl-2-phthaloylaminopropanal in 1.5 ml of THF was added, at 0° C., 0.27 ml (5 mmol) of nitromethane, followed by dropwise addition of 0.1 ml (0.16 mmol) of a 1.6N n-butyllithium solution in n-hexane. The resultant mixture was stirred at 0° C. for 2 hours. To this solution were added 0.3 ml of 1N hydrochloric acid and 3 ml of water. The mixture was extracted with diethyl ether, and the extract was washed with a saturated aqueous solution of sodium chloride and dried over anhydrous sodium sulfate. The solvent was distilled off under reduced pressure and the residue was analyzed by HPLC in the same manner as in Example 3 to determine the yield and diastereomer ratio of the product. Yield 84%; [(2S,3S):(2R,3S)] (*2R,3S*):(*2S,3S*)=73:27.

Examples 32 and 33

The procedure of Example 31 was, followed using two other reaction solvents. The results obtained are shown in Table 5.

TABLE 5

| | Solvent | % yield | [(2S, 3S):(2R, 3S)] (2R, 3S):(2S, 3S) |
|---|---|---|---|
| Example 32 | Toluene | 87 | 76:24 |
| Example 33 | Methylene chloride | 85 | 76:24 |

Example 34

To a mixture of 0.58 ml of nitromethane and 10 ml of THF was added dropwise gradually 2.24 ml of a 1.6N n-butyllithium solution in n-hexane with stirring at −78° C. After completion of the dropping, the mixture was further stirred at −78° C. for 30 minutes and, then, a solution of 1.0 g (0.25 mmol) of (S)-3-phenyl-2-phthaloylaminopropanal in 5.0 ml of THF was added dropwise. The resultant mixture was stirred at −78° C. for 5 hours. To this solution were added 8 ml of 1N hydrochloric acid and 20 ml of water. The mixture was extracted with diethyl ether, the extract was washed with a saturated aqueous solution of sodium chloride and dried over anhydrous sodium sulfate, add the solvent was distilled off under reduced pressure. The residue was analyzed by HPLC in the same manner as in Example 3 to determine the yield and diastereomer ratio of the product. Yield 63%; [(2S,3S):(2R,3S)] (*2R,3S*):(*2S,3S*)=90:10.

Example 35

Synthesis of (2S,3S)-phenylnorstatine hydrochloride [(2S, 3S)] (*2R,3S*)-1-Nitro-4-phenyl-3-phthaloylamino-2-butanol (300 mg, 0.882 mmol) was heated in 3.0 ml of 12N concentrated hydrochloric acid with stirring at 100° C. for 46 hours. After the 46 hours period, the mixture was cooled to room temperature, the insoluble matter was filtered off, and the filtrate was washed with three portions of methylene chloride. The aqueous layer was concentrated to dryness under reduced pressure, followed by furthest drying under vacuum (0.5 torr, room temperature, 12 hours). There was obtained 202 mg of (2S,3S)-phenylnorstatine hydrochloride (yield: 99%).

(2S,3S)-phenylnorstatine hydrochloride:

IR (Nujol)ν($cm^{-1}$): 3300, 2800–3200, 1730

$^1$H-NMR (400 MHz, $D_2O$)δ(ppm): 2.95 (1H, dd, J=14.4, 9.0 Hz), 3.08 (1H, dd, J=14.4, 6.1 Hz), 4.07–4.12 (1H, m), 4.63 (1H, d, J=11.2 Hz), 7.32–7.44 (5H, m)

$^{13}$C-NMR (100 MHz, $CD_3OD$)δ(ppm): 34.9, 56.7, 71.1, 129.1, 130.6, 130.9, 173.8

Example 36

Synthesis of (2R,3S)-phenylnorstatine hydrochloride

[(2R,3S)] (*2S,3S*)-1-Nitro-4-phenyl-3-phthaloylamino-2-butanol (100 mg, 0,294 mmol) was heated in 1.0 ml of 12N concentrated hydrochloric acid with stirring at 100° C. for 46 hours. After the 46 hours period, the mixture was cooled to room temperature, the insoluble matter was filtered off, and the filtrate was washed with three portions of methylene chloride. The aqueous layer was concentrated to dryness under reduced pressure, followed by further drying under vacuum (0.5 torr, room temperature, 12 hours). There was obtained 54 mg of (2R, 3S)-phenylnorstatine hydrochloride (yield: 80%).

(2R,3S)-Phenylnorstatine hydrochloride:

IR (Nujol)ν($cm^{-1}$): 3300, 2800–3200, 1740

$^1$H-NMR (400 MHz, $D_2O$)δ(ppm): 3.03 (1H, dd, J=14.2, 7.8 Hz), 3.16 (1H, dd, J=14.2, 7.8 Hz), 3.97 (1H, dt, J=7.8, 3.4 Hz), 4.38 (1H, d, J=3.4 Hz), 7.36–7.47 (5H, m)

Example 37

Synthesis of [(2S,3R)] (*2R,3R*)-3-t-butoxycarbonylamino-1-nitro-4-phenyl-2-butanol To a stirred solution of 62.3 mg (0.25 mmol) of (R)-2-t-butoxycarbonylamino-3-phenylpropanal [synthesized by the method described in Journal of Medicinal Chemistry, 130, 1162 (1987)] in 1.0 ml of THF was added at 0° C., 0.27 ml (5 mmol) of nitromethane, followed by dropwise addition of 0.5 ml (0.025 mmol) of the lanthanum/(R)-1,1'-bi-2-naphthol complex solution (Reference Example 1, 0.05 mol/l). The resultant mixture was stirred at 0° C. for 2 hours. To this solution were added 0.5 ml of 1N hydrochloric acid and 3 ml of water. The mixture was extracted with diethylether, the extract was washed with a saturated aqueous solution of sodium chloride and dried over anhydrous sodium sulfate, and the solvent was distilled off under reduced pressure. The residue was purified by silicagel column chromatography (eluent; n-hexane-ethyl acetate 8:2) to give 47 mg of [(2S,3R)] (*2R,3R*)-3-t-butoxycarbonylamino-1-nitro-4-phenyl-2-butanol. Yield 60%. [(2S,3R)] (*2R,3R*)-3-t-Butoxycarbonylamino-1-nitro-4-phenyl-2-butanol:

IR (Nujol)ν($cm^{-1}$): 3374, 1670, 1528, 1165

$^1$H-NMR (400 MHz, $CDCl_3$)δ(ppm): 1.41 (9H, s), 2.8–3.0 (2H, m), 3.55 (1H, bs), 3.81 (1H, dd, J=16.1, 7.8 Hz), 4.30 (1H, bs), 4.4–4.5 (2H, m), 4.93 (1H, dm, J=9.3 Hz), 7.2–7.4 (5H, m)

$^{13}$C-NMR (100 MHz, $CDCl_3$)δ(ppm): 28.2, 38.1, 53.9, 68.4, 79.2, 80.3, 126.8, 128.7, 129.2, 137.2, 155.9

Example 38

Synthesis of (2S,3R)-phenylnorstatine hydrochloride

[(2S,3R)] (*2R,3R*)-3-t-Butoxycarbonylamino-1-nitro-4-phenyl-2-butanol (40 mg, 0.129 mmol) was heated in 1.0 ml of 12N concentrated hydrochloric acid with stirring at 100° C. for 40 hours. The reaction mixture was cooled to room temperature, the insoluble matter was filtered off, and the filtrate was washed with three portions of methylene chloride. The aqueous layer was concentrated to dryness under reduced pressure, followed by further drying under vacuum (0.5 torr, room temperature, 12 hours). There was obtained 25 mg of (2S, 3R)-phenylnorstatine hydrochloride (yield 85%).

(2S,3R)-Phenylnorstatine hydrochloride:

IR (Nujol)ν: 3300, 2800–3200, 1740

$^1$H-NMR (400 MHz, $D_2O$)δ(ppm): 3.03 (1H, dd, J=14.2, 7.8 Hz), 3.16 (1H, dd, J=14.2, 7.8 Hz), 3.97 (1H, dr, J=7.8, 3.4 Hz), 4.38 (1H, d, J=3.4 Hz), 7.36–7.47 (5H, m)

INDUSTRIAL APPLICABILITY

In accordance with the present invention, a production method of commercial value can be provided by which only one of the four optical isomers of phenylnorstatine as selected arbitrarily can be produced in high yields in a simple and easy manner without any substantial hazard.

We claim:

1. An 3-amino-1-nitro-4-phenyl-2-butanol derivative of the general formula (1)

(1)

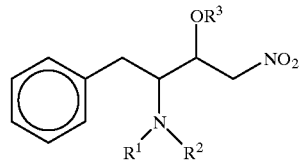

wherein $R^1$ and $R^2$ each independently represents a hydrogen atom or an amino group protecting group and $R^3$ represents a hydrogen atom or a hydroxy group protecting group.

2. A compound as claimed in claim 1, wherein, in general formula (1), $R^3$ is a hydrogen atom and the amino group protecting group is a phthaloyl group.

3. A compound as claimed in claim 1, wherein, in general formula (1), $R^3$ is a hydrogen atom and the amino group protecting group is a t-butoxycarbonyl group.

4. A compound as claimed in claim 1, wherein the general formula (1) has the [(2S,3S)] (*2R,3S*)-erythro form configuration.

5. A compound as claimed in claim 1, wherein the general formula (1) has the [(2S,3R)] (*2R,3S*)-threo form configuration.

6. A method of producing 3-amino-1-nitro-4-phenyl-2-butanol derivatives of the general formula (1)

(1)

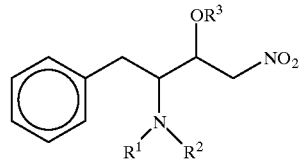

wherein $R^1$ and $R^2$ each independently represents a hydrogen atom or an amino group protecting group and $R^3$ represents a hydrogen atom or a hydroxy group protecting group, which comprises reacting an amine aldehyde of the general formula (2)

(2)

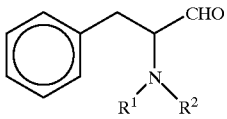

wherein $R^1$ and $R^2$ are as defined above, with nitromethane in the presence of a base.

7. A method of stereoselectively producing [(2S,3S)] (*2R,3S*)-3-amino-1-nitro-4-phenyl-2-butanol derivatives of the general formula (4)

(4)

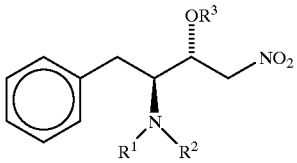

wherein $R^1$ in combination with $R^2$ represents a phthaloyl group and $R^3$ is a hydrogen atom, which comprises reacting an (S)-aminoaldehyde derivative of the general formula (3)

(3)

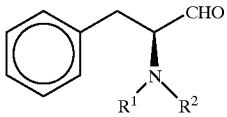

wherein $R^1$ and $R^2$ are as defied above, with nitromethane in the presence of a base.

8. A method of stereoselectively producing [(2S,3R)] (*2R,3R*)-3-amino-1-nitro-4-phenyl-2-butanol derivatives of the general formula (6)

(6)

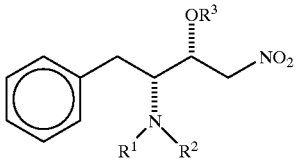

wherein $R^1$ is a hydrogen atom and $R^2$ represents a t-butoxycarbonyl group and $R^3$ is a hydrogen atom, which comprises reacting an (R)-aminoaldehyde derivative of the general formula (5)

(5)

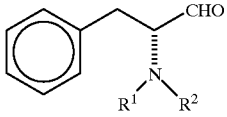

wherein $R^1$ and $R^2$ are as defined above, with nitromethane in the presence of a base.

9. A method as claimed in claim 6 wherein the base is an alkali metal alkoxide.

10. A method as claimed in claim 9, wherein the alkali metal alkoxide is a compound of the general formula (7)

(7)

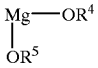

wherein $R^4$ and $R^5$ each represents an alkyl group containing 1 to 6 carbon atoms.

11. A method as claimed in claim 6 wherein the base is a compound of the general formula (8)

$$R^7Li \tag{8}$$

wherein $R^7$ represents an aryl group or an alkyl group containing 1 to 6 carbon atoms.

12. A method as claimed in claim 6 wherein the base is a complex prepared from a compound of the general formula (9)

$$MX_3 \tag{9}$$

wherein M represents a rare earth atom and X represents a halogen atom, and 1,1'-bi-2-naphthol or the lithium salt thereof.

13. A method as claimed in claim 12, wherein the complex is one prepared from lanthanum trichloride and (R)-1,1'-bi-2-naphthol.

14. A method as claimed in claim 6 wherein the base is a complex prepared from a compound of the general formula (10)

$$M(OR^8)_3 \tag{10}$$

wherein M represents a rare earth atom and R8 represents a substituted alkyl group containing 1 to 8 carbon atoms, and 1,1'-bi-2-naphthol or the lithium salt thereof.

15. A method as claimed in claim 14, wherein the complex is one prepared from lanthanum triisopropoxide and the lithium salt of (R)-1,1'-bi-2-naphthol.

16. A method of producing compounds of the general formula (11)

(11)

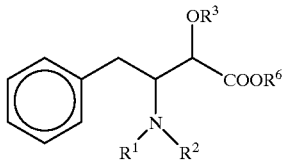

wherein $R^1$ and $R^2$ each independently represents a hydrogen atom or an amino group protecting group, $R^3$ represents a hydrogen atom or a hydroxy group protecting group and $R^6$ represents a hydrogen atom or an alkyl group containing 1 to carbon atoms, or salts thereof which comprises treating an 3-amino-1-nitro-4-phenyl-2-butanol derivative of the general formula (1)

(1)

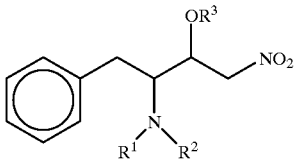

wherein $R^1$, $R^2$ and $R^3$ are as defined above, with an acid.

17. A method as claimed in claim 16, wherein the general [formulas] *formula* (1) [and] *has the* (*2R,3S*)-*erythro form configuration and the compound of general formula* (11) [each] has the (2S,3S)-erythro form configuration and the amino group protecting group is a phthaloyl group.

18. A method as claimed in claim 16, wherein the general [formulas] *formula* (1) [and] *has the* (*2R,3S*)-*threo form configuration and the compound of general formula* (11) [each] has the (2S,3R)-threo form configuration and [tile] *the* amino group protecting group is a t-butoxycarbonyl group.

19. A method of producing compounds of the general formula (11)

(11)

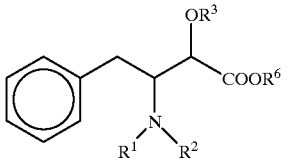

wherein $R^1$ and $R^2$ each independently represents a hydrogen atom or an amino group protecting group, $R^3$ represents a hydrogen atom or a hydroxy group protecting group and $R^6$ represents a hydrogen atom or an alkyl group containing 1 to 6 carbon atoms, or salts thereof which comprises reacting an aminoaldehyde derivative of the general formula (2)

(2)

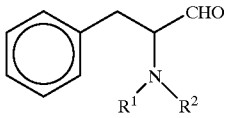

wherein $R^1$ and $R^2$ are as defined above, with nitromethane in the presence of a base and treating the resulting 3-amino-1nitro-4-phenyl-2-butanol derivative of the general formula (1)

(1)

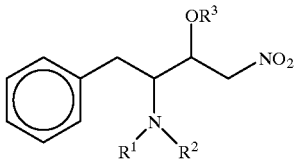

wherein $R^1$, $R^2$ and $R^3$ are as defined above, with an acid.

20. The method as claimed in claim 19, wherein said base is a complex prepared from a compound of the general formula (9)

$$MX_3 \quad (9)$$

wherein M represents a rare earth atom and X represents a halogen atom, or a compound of the general formula (10)

$$M(OR^8)_3 \quad (10)$$

wherein M is as defined above and $R^8$ represents a substituted alkyl group containing 1 to 8 carbon atoms, and 1,1'-bi-2-naphthol or the lithium salt thereof.

21. The method as claimed in claim 20, wherein said derivative of the general formula (1) is 1-nitro-4-phenyl-3-phthaloylamino-2-butanol having the erythro configuration or phenylnorstatine having the erythro configuration from optically active 3-phenyl-2-phthaloylamino propanol.

22. The method as claimed in claim 21, wherein the optically active 3-phenyl-2-phthaloylaminopropanal is the (2S) form, the 1-nitro-4-phenyl-3-phthaloylamino-2-butanol having the erythro configuration is the [(2S,3S)] (*2R,3S*) form and the phenylnorstatine having the erythro configuration is the (2S,3S) form.

23. The method as claimed in claim 20, wherein said derivative of the general formula (1) is 3-t-butoxycarbonyl amino-1-nitro-4-phenyl-2-butanol having the threo configuration or phenylnorstatine having the threo configuration from optically active 2-t-butoxycarbonyl amino-3-phenylpropanal.

24. The method as claimed in claim 23, wherein the optically active 2-t-butoxycarbonylamino-3-phenylpropanal is the (2R) form, the 3-t-butoxycarbonylamino-1-nitro-4-phenyl-2-butanol having the threo configuration is the [(2S,3R)] (*2R,3R*) form and the phenylnorstatine having the threo configuration is the (2S,3R) form.

* * * * *